US00PP23755P3

(12) United States Plant Patent
Lewis

(10) Patent No.: US PP23,755 P3
(45) Date of Patent: Jul. 23, 2013

(54) ***STYRAX* PLANT NAMED 'JLWEEPING'**

(50) Latin Name: *Styrax Japonicus*
Varietal Denomination: JLWeeping

(76) Inventor: John Lewis, Salem, OR (US)

( * ) Notice: Subject to any disclaimer, the term of this patent is extended or adjusted under 35 U.S.C. 154(b) by 0 days.

(21) Appl. No.: 13/065,105

(22) Filed: Mar. 14, 2011

(65) Prior Publication Data

US 2012/0240298 P1 Sep. 20, 2012

(51) Int. Cl.
*A01H 5/00* (2006.01)

(52) U.S. Cl.
USPC ..... Plt./216

(58) Field of Classification Search
USPC ..... Plt./216
See application file for complete search history.

(56) References Cited

U.S. PATENT DOCUMENTS

PP19,664 P2 * 1/2009 Silva ..... Plt./216

* cited by examiner

*Primary Examiner* — June Hwu
(74) *Attorney, Agent, or Firm* — Chernoff Vilhauer LLP

(57) ABSTRACT

A new cultivar of *Styrax* plant named JLWEEPING that is characterized by the combination of a weeping habit, pink flowers and leaves which are slightly larger, glossier and less pubescent than other known varieties.

4 Drawing Sheets

Genus: *Styrax*.
Species: *Japonicus*.
Varietal denomination: JLWeeping.

BACKGROUND OF THE INVENTION

The present invention relates to a new and distinct cultivar of *Styrax japonicus*, or weeping Japanese snowbell, that is grown for use as a small tree. It is known botanically as *Styrax japonicus* and will be referred to hereinafter by the cultivar name 'JLWEEPING'. The plant was discovered as a seedling of unknown parentage growing with *Styrax japonicus* seedlings in a liner bed row in the JLPN nursery in Salem, Oreg.

The new variety is distinguished from known Japanese snowbell varieties because of the following combination of characteristics: the growth habit is weeping in form and differs significantly from the species which is rounded to broad-rounded with a horizontal branching appearance. While its shape is similar to another weeping cultivar, 'Fragrant Fountains', U.S. Pat. No. 19,664, it forms pink flowers which are slightly fragrant. Additionally, it forms leaves which are slightly larger in length and width, are darker green and glossy, and whose undersides have pubescence only along the veins.

Plants of the new variety have been asexually reproduced in Salem, Oreg., USA, through the use of softwood cuttings or graftings on *Styrax japonicus* understock. The characteristics of the new variety have been found to be strictly transmittable by such asexual repropagation, and the new cultivar reliably reproduces in a true to type manner from one generation to another.

BRIEF SUMMARY OF THE INVENTION

The following traits have been repeatedly observed and represent the characteristics of the subject variety. These traits in combination distinguish the variety from other varieties known to the inventor.

The subject plant exhibits a combination of a weeping habit, pink flowers, and leaves which are slightly larger, glossier, and less pubescent than other known varieties.

Plants of the subject variety have not been observed under all possible environmental conditions. Accordingly, it is possible that phenotypic expressions may vary somewhat with changes in light intensity and duration, cultural practice, and other environmental conditions.

DETAILED BOTANICAL DESCRIPTION OF PREFERRED EMBODIMENT

The chart used in the identification of color is The R.H.S. Color Chart of The Royal Horticultural Society, London, England. Other reference to color is to be accorded its ordinary dictionary significance. The description is based upon the observation of plants of the new variety having an age of approximately 4 years while being grown outdoors at Salem, Oreg., U.S.A.

Figure 1:
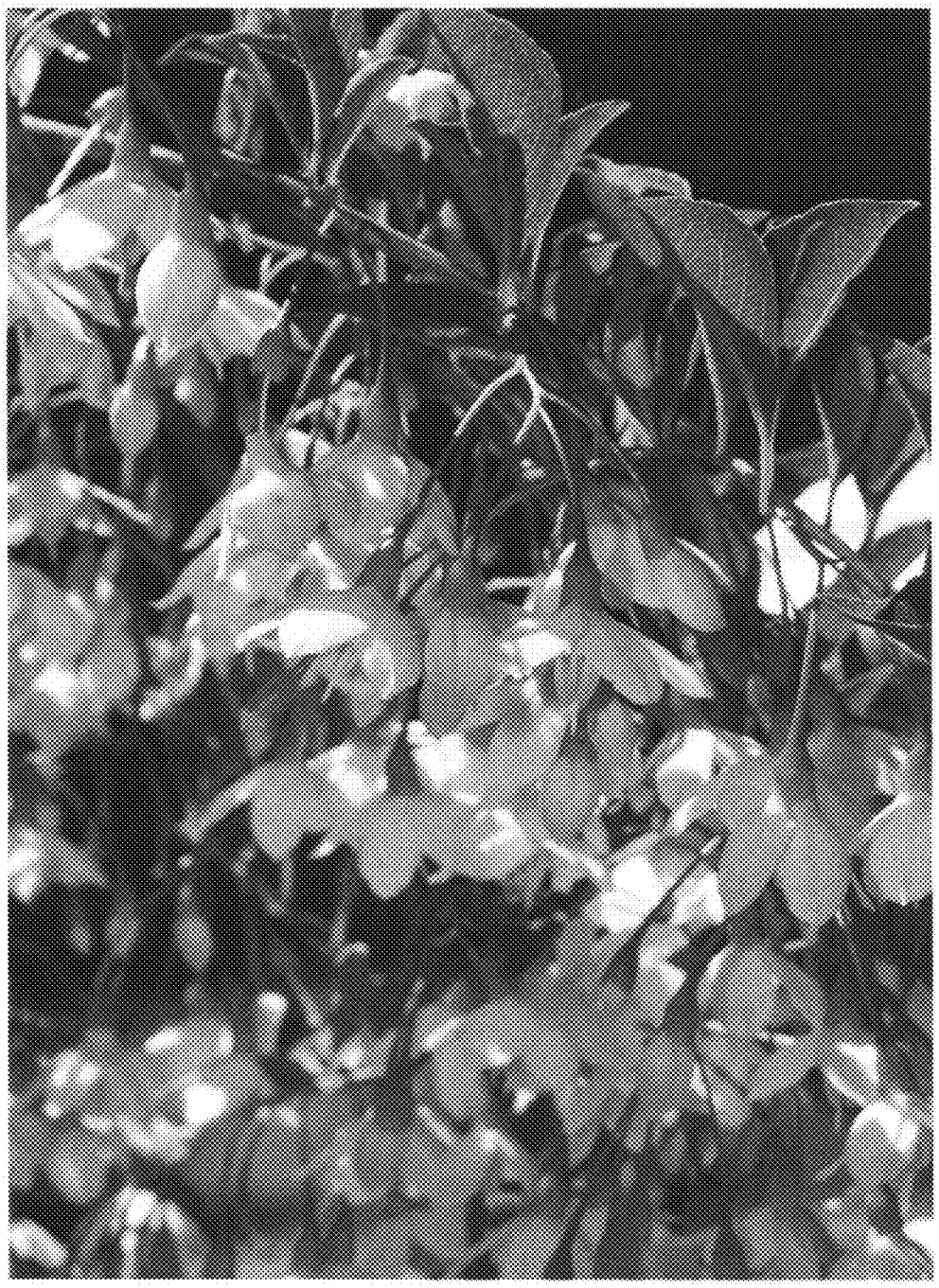
FIG. 1 is a close-up view of a 4 year old specimen of the new variety, top grafted on a 36" standard.
Figure 2:
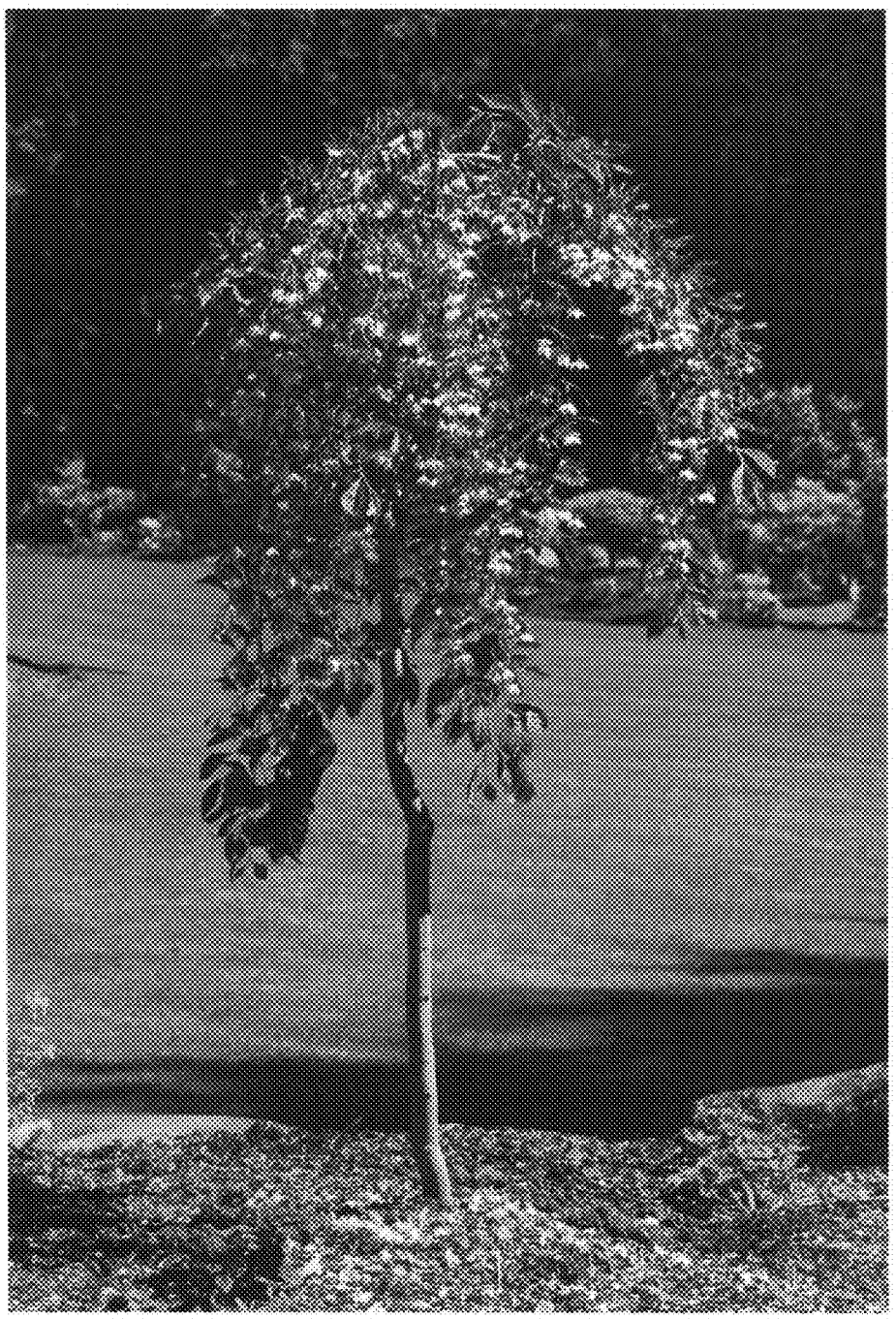
FIG. 2 is the same 4 year old, top grafted specimen, but from a distance to show the pendulous habit of the new variety.

The new variety exhibits extremely pendulous growth habit with a medium growth rate as shown in FIGS. 1 and 2 in this regard. When top-grafted, the tree is approximately six feet tall and has a spread of approximately 30 inches. When propagated by softwood cutting, it can be pruned to the desired height and spread.

The vegetative parts of the new variety are typical of the genus except as specifically indicated hereafter. The alternate, simple leaves are broadly elliptical with serrated margins, an acuminate apices and cuneate base. See FIG. 3 in this regard. The petiole is approximately ⅜" in length compared to the typical ⅓" of the species. The petiole is smooth, non-glossy and the color is Green Group 143A. The species leaves are normally 1 to 3½" long and ½ to 1½" wide. The new variety has leaves approximately 3½ to 4" in length and around 2 to 2½" in width. Compared to another weeping variety, 'Fragrant Fountains', its leaves are much larger, darker in color and glossier. 'Fragrant Fountain' has a light pubescence along the entire underside of its leaves unlike the new 'JLWeeping' variety which only has pubescence along the veins.

The emerging leaves of the new variety in the spring on the upper surface are like Green Group 144A. As leaves mature, they deepen to Green Group 139A with an underside of Green Group 137C. Leaf venation is Yellow-Green Group 147C.

Immature twigs are smooth, non-glossy, Yellow Green Group 144B. Mature twigs are coarse, striped lengthwise, Greyed-Orange Group 175C, Grey-Brown Group 199D. Bark is smooth Greyed-Green Group 198C.

Buds are ½" long, 7/32" wide. The upper surface is Red-Purple Group 65C. The lower surface is Red-Purple Group 65B.

The blossom appearance of the new variety is similar to that of the genus. The new variety forms in profusion attractive pink blossoms which, while in bud generally correspond to the color of Red-Purple Group 65A, opening to Red-Purple Group 65 B, C & D. The bloom stem ranges in color from Red-Purple Group 60A, B & C. The color of the upper and lower surface is the same. The petal is elliptical, the apex acute and the base oblique. There are 13 flowers per pendulous stalk on average.

Figure 3:
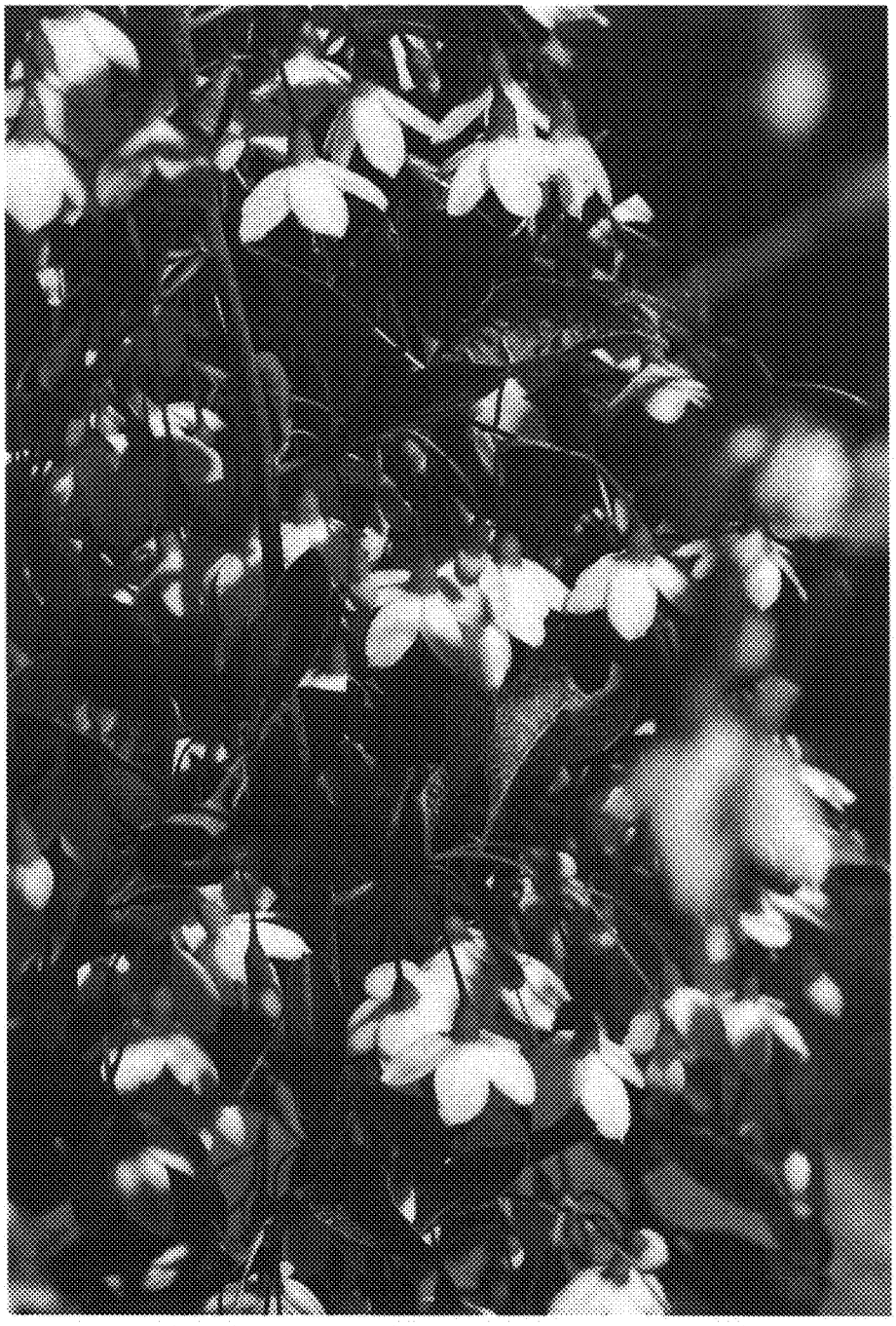
FIG. 3 is the leaves, flower and flower bud of the new variety.
Figure 4:
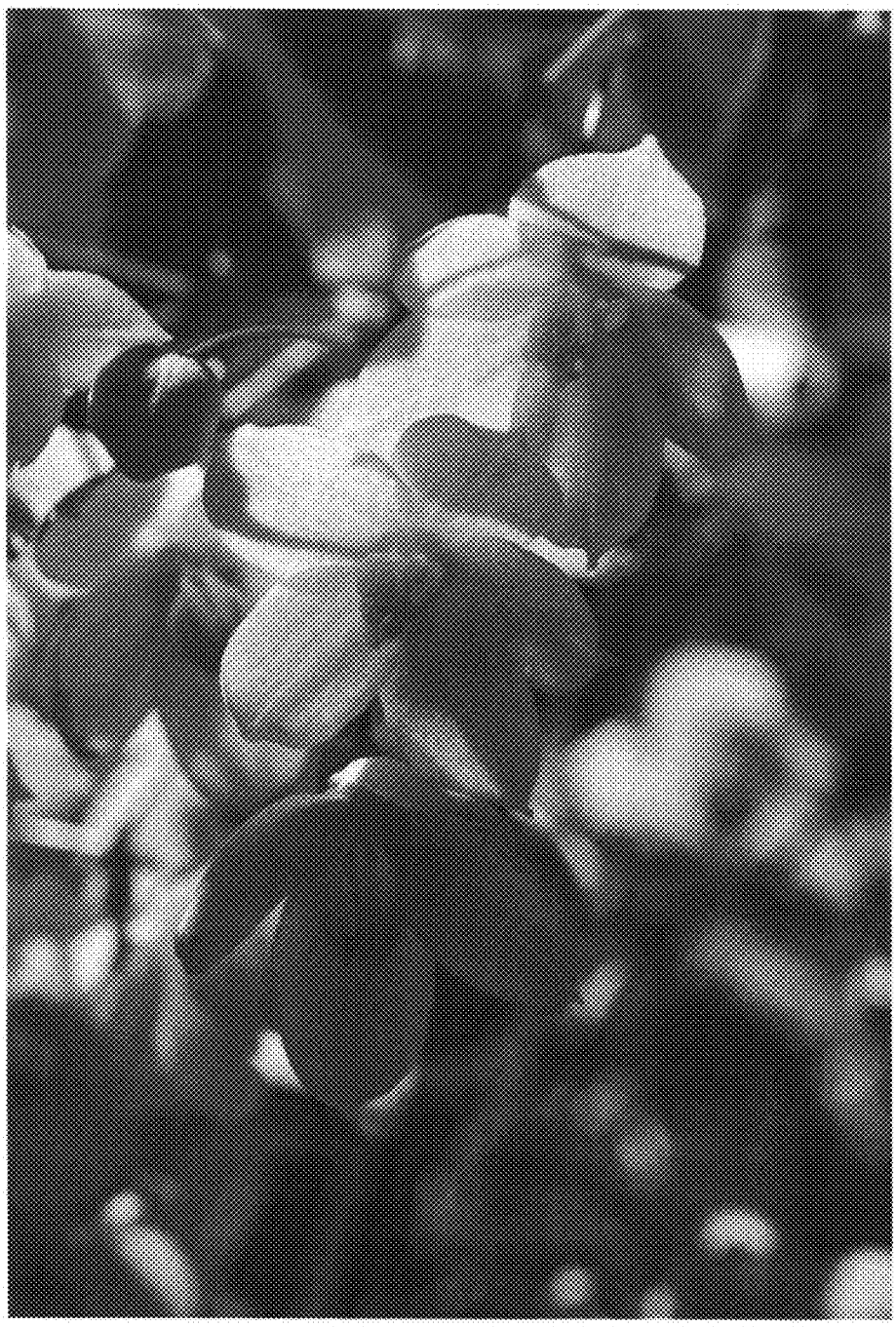
FIG. 4 is a close view of the flowers of the new variety.

The overall configuration of the flowers is generally typical of the genus. The flowers are perfect, pink, bell-shaped and numerous. Blossoming commonly occurs during mid-May to Mid-June at Salem, Oreg., U.S.A., where it commonly extends over approximately 3 to 4 weeks depending upon the weather conditions that are encountered. The flowers are commonly borne on a 1 to 1½" long pendulous stalk, occurring on short lateral shoots, each shoot has multiple flowers which are lightly fragrant. As shown in FIGS. 3 & 4, the blossoms are corolla 4-6 lobed being united near the base, with the margins having a slight ruffle at times. The reproductive organs are typical of a *Styrax japonicus* and other species and cultivars angiosperm flowering plant. One pistil per flower, ⅜" long, Yellow Group 4B and Yellow-Orange Group 15A. Ten stamens per flower, 9/16" long, White Group 155D. The anthers are Yellow Group 15A in coloration. Calyx is campanulate, 3/16" long, ⅛" wide, Red-Purple Group 64C.

During observations to date, fruit has been formed and is not considered to be ornamental in nature. It forms a dry ovoid, about ½" long, apparent in August and falling around November which is typical of the species. Fruit is Yellow-Green Group 148D.

When grown at Salem, Oreg., U.S.A., the new variety has exhibited disease resistance under observations to date and has not been affected to any degree by common *Styrax* diseases or by insects which commonly attack *Styrax*. The new variety has proven to be hardy when tested in U.S.D.A. Hardiness Zone 5.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A new and distinct cultivar of *Styrax* plant named JLWEEPING, as described and illustrated herein.

* * * * *